(12) United States Patent
Tamai et al.

(10) Patent No.: US 6,802,608 B1
(45) Date of Patent: Oct. 12, 2004

(54) LOW VISION MEASURING INSTRUMENT

(75) Inventors: Makoto Tamai, 2-22-18,
Yagiyamahoncho, Taikhaku-ku,
Sendai-shi, Miyagi 982-0801 (JP);
Masao Yoshikawa, Aichi (JP)

(73) Assignee: Makoto Tamai (JP)

( * ) Notice: Subject to any disclaimer, the term of this patent is extended or adjusted under 35 U.S.C. 154(b) by 287 days.

(21) Appl. No.: 10/168,369

(22) PCT Filed: Oct. 6, 2000

(86) PCT No.: PCT/JP00/06985

§ 371 (c)(1),
(2), (4) Date: Jun. 19, 2002

(87) PCT Pub. No.: WO02/30272

PCT Pub. Date: Apr. 18, 2002

(51) Int. Cl.[7] .............................. A61B 3/14; A61B 3/00
(52) U.S. Cl. ...................... 351/209; 351/246; 600/558
(58) Field of Search ................................ 351/200, 205, 351/209, 210, 211, 212, 213–218, 221–224, 237, 246; 600/558, 4–6

(56) References Cited

U.S. PATENT DOCUMENTS

| | | | | |
|---|---|---|---|---|
| 4,334,739 A | * | 6/1982 | Seckinger ................... 351/246 |
| 5,589,897 A | * | 12/1996 | Sinclair et al. ............. 351/223 |
| 5,805,270 A | * | 9/1998 | Marshall ...................... 351/222 |
| 5,805,271 A | * | 9/1998 | Kirschbaum et al. ....... 351/224 |
| 5,864,385 A | * | 1/1999 | Gonzales de la Rosa ... 351/246 |

FOREIGN PATENT DOCUMENTS

JP 2000-287927 10/2000

* cited by examiner

Primary Examiner—Brian L. Casler
Assistant Examiner—John R Sanders
(74) Attorney, Agent, or Firm—Hayes Soloway P.C.

(57) ABSTRACT

Light is emitted to each of right and left eyes, the emission of light is controlled according to light stimulation steps defined by a combination of light intensities and light emission times, and presence or absence of reaction of a test subject to light is detected at the respective stimulation steps. When reactions, the number of times of occurrence of which is a predetermined number of times of occurrence and less, are detected at a given stimulation step, the given stimulation step is regarded as not being viewed, and tests are omitted which would be effected at stimulation steps lower than the given stimulation step by a predetermined number of steps, whereas when reactions, the number of times of occurrence of which is a predetermined number of times of occurrence and more, are detected at a given stimulation step, the given stimulation step is regarded as being viewed, and tests are omitted which would be effected at stimulation steps higher than the given stimulation step by a predetermined number of steps.

11 Claims, 8 Drawing Sheets

FIG. 2
(a) 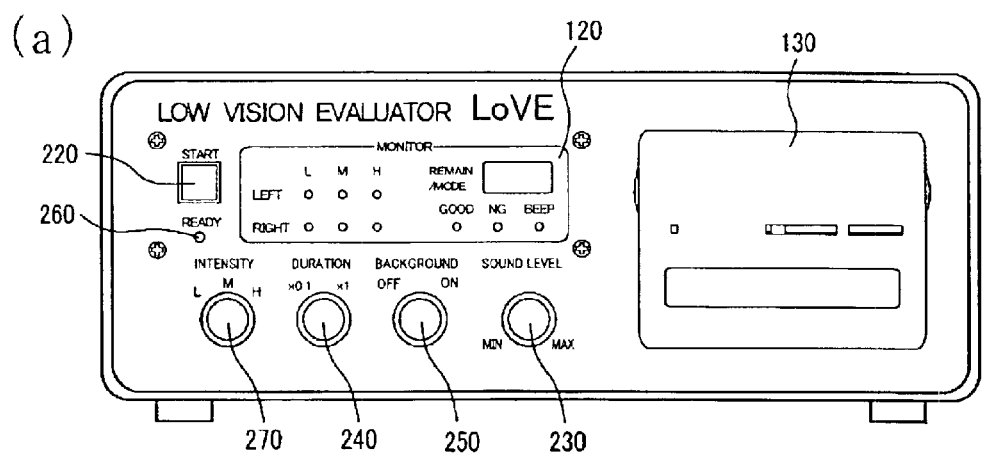
(b) 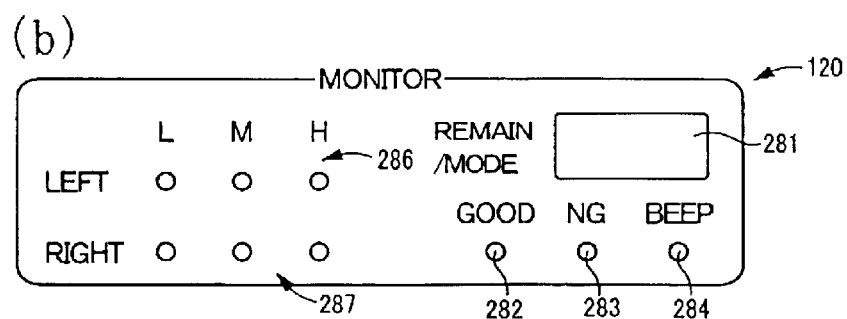
(c) 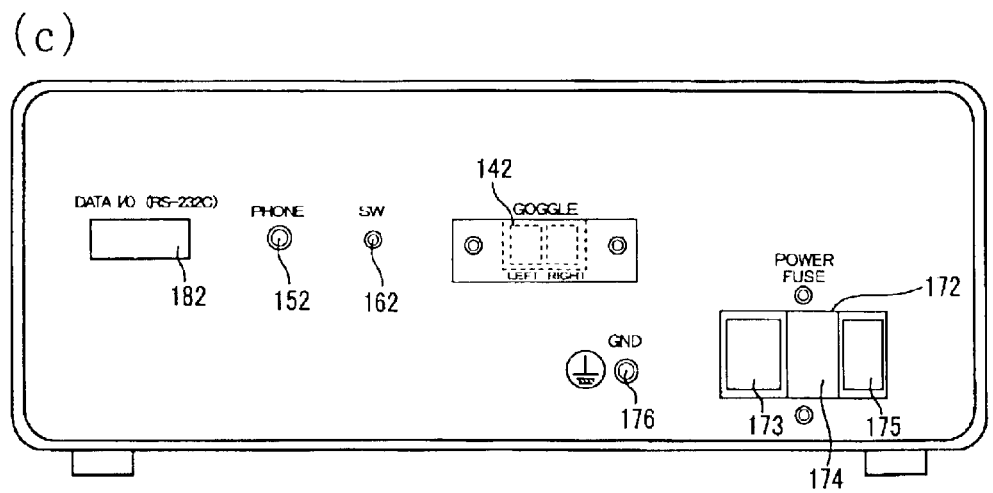

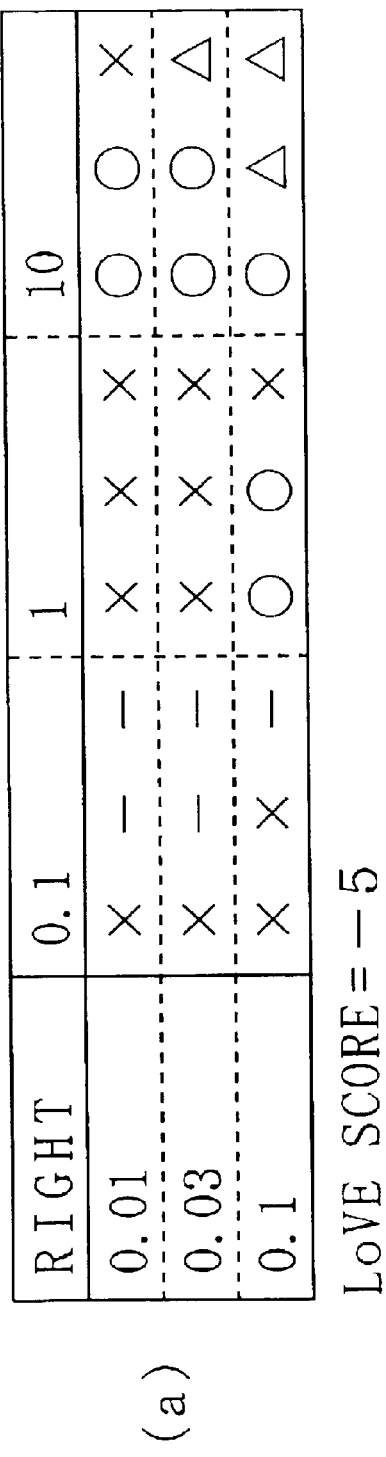
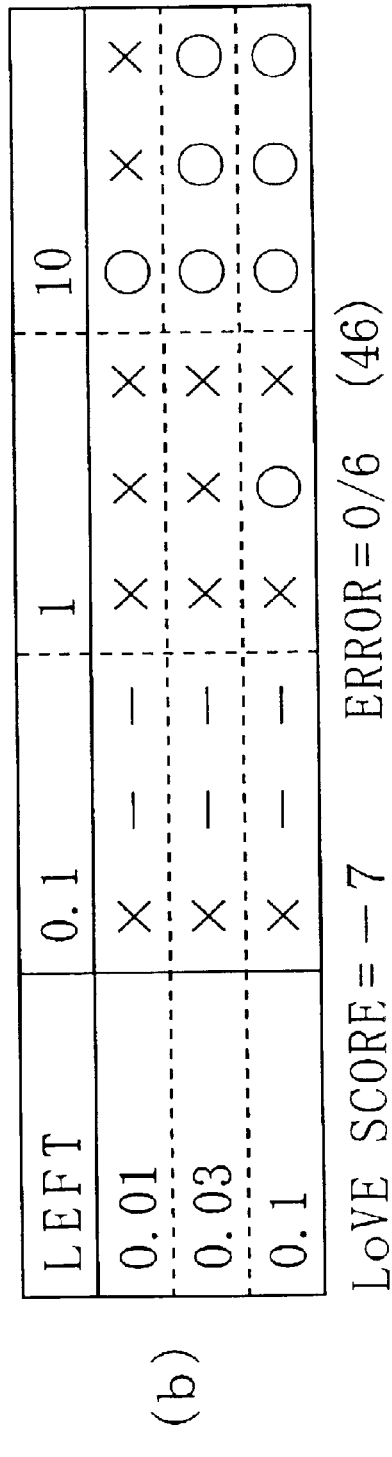
FIG. 5
EXAMPLE OF RESULT OF TEST    STIMULATION ; 0.1, 1, 1, 10cd/m²

FIG. 6  RESULT OF TEST OF STIMULATION INTENSITY L (LoVE SCORE = −7)

FIG. 7
(a)
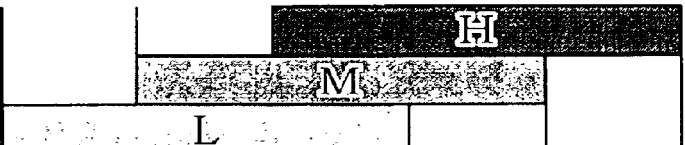
(b)
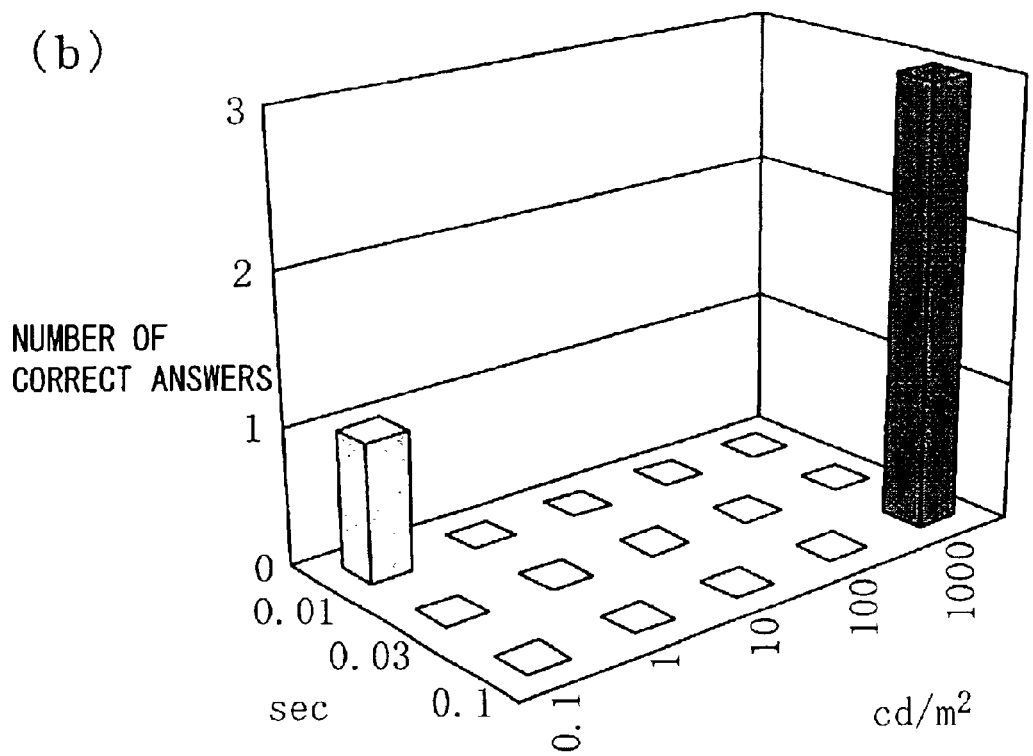
LoVE SCORE = −14

LOW VISION MEASURING INSTRUMENT

CROSS-REFERENCE TO RELATED APPLICATIONS

This present application is a national stage filing under 371 claiming benefit of international application No. PCT/JP00/06985, filed Oct. 26, 2000.

TECHNICAL FIELD

The present invention relates to measurement capable of evaluating poor eyesight by classifying grades of poor eyesight, and more particularly, to measurement which reduces a burden on a test subject.

BACKGROUND ART

When illnesses such as pigmentary degeneration of retina and the like become serious and eyesight cannot be represented by a numeral (in which an object of 0.1 at a distance of 50 cm cannot be read), it is evaluated by three steps, that is, by a finger counting test (a test subject counts the number of tester's fingers shown in front of his or her eyes), a moving finger sensing test (a test subject recognizes fingers moving in front of his or her eyes), and a light sensing test (when a test subject cannot recognize even moving fingers, he or she determines brightness and darkness in a dark room with light irradiated to her or her pupil), based on rational symptom. When a patient of this kind of illness is treated, or when it is intended to evaluate a progress of the illness in detail, evaluation effected at the three steps is too rough to indicate a change of the illness. Further, strong stimulation of eyes with strong light for measurement may damage visual cells.

To cope with the above problem, there is available a measuring method employing a tester using stimulation light emitted from a white LED (for example, "Classification of Grades of Very Poor Eyesight and Development of Measuring Instrument for Very Poor Eyesight by Hikoshi Kunikata, Masahiro Tsunoda, and Sin Tamai, Journal of Japanese Ophthalmological Society, Vol. 102, extra-edition, p152, 1998). However, the tester has a problem that a large burden is applied to a test subject.

DISCLOSURE OF THE INVENTION

An object of the present invention to accurately measure eyesight of a person having poor eyesight with a small burden on a test subject.

To achieve the object, the present invention is a poor eyesight measuring instrument which is characterized by comprising light emission means for emitting light to each of right and left eyes; light emission control means for controlling the light emission means according to light stimulation steps defined by a combination of light intensities and light emission times; and means for detecting presence or absence of reaction of a test subject to light at the respective stimulation steps, wherein, the light emission control means controls selection of the stimulation steps at random in a series of tests effected a prescribed number of times at each stimulation step; when the light emission control means detects reactions, the number of times of which is a predetermined number of times and less, at a given stimulation step, the light emission control means regards the given stimulation step as not being viewed and omits tests which would be effected at stimulation steps lower than the given stimulation step by a predetermined number of steps; and when the light emission control means detects reactions, the number times of which is a predetermined number of times and more, at a given stimulation step, the light emission control means regards the given stimulation step as being viewed and omits tests which would be effected at stimulation steps higher than the given stimulation step by a predetermined number of steps.

Further, the poor eyesight measuring instrument may comprise means for outputting a total number of the not viewed stimulation steps as an evaluation of poor eyesight.

The light emission means may emit white light and further may emit the three primary colors of red, green, and blue. The light emission means may comprise an LED, a liquid crystal, and a cathode ray tube, and the like. Further, the light emission means further comprises backlight emission means for emitting backlight.

Further, the poor eyesight measuring instrument comprises means for giving a sign, and the light emission control means controls light emission so that light is emitted after a sign is given. At that time, the light emission control means may include control for not emitting light after a sign is given. A sound and other sensible stimulation may be used as the sign.

A method effected by the instrument is also included in the present invention.

BRIEF DESCRIPTION OF THE DRAWINGS

FIG. 2 is a view showing an outside view of the poor eyesight measuring instrument of the present invention;

FIG. 5 is a view showing a result of measurement effected by the poor eyesight measuring instrument;

FIG. 7 shows views illustrating examples representing a result of measurement effected by the poor eyesight measuring instrument of the present invention by graphs.

BEST MODE FOR CARRYING OUT THE INVENTION

A best mode for carrying out the present invention will be described below with reference to the drawings.

Figure 1:
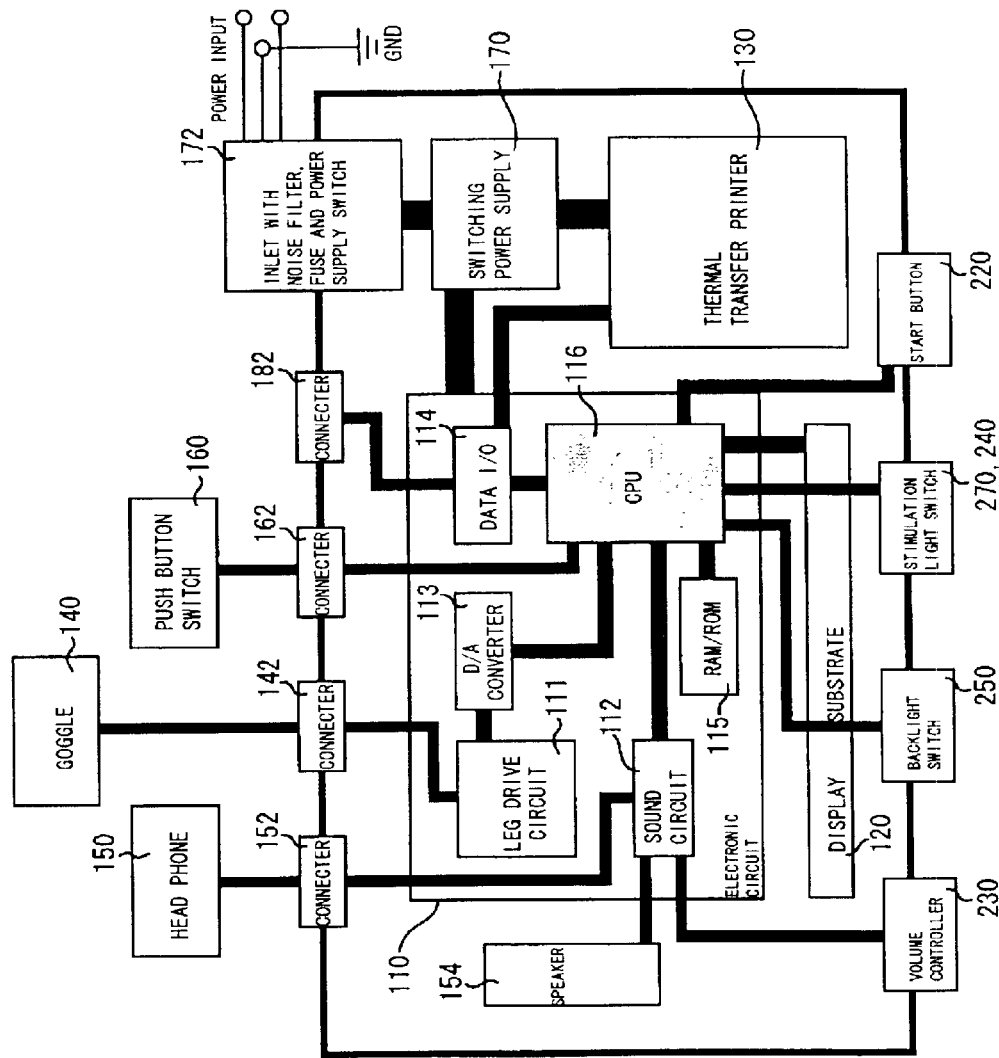
FIG. 1 is a block diagram showing a construction of a poor eyesight measuring instrument of the present invention.

FIG. 1 shows an example of a construction of an embodiment of a measuring instrument of the present invention composed of a microprocessor in which light stimulation is applied to a test subject after a sound is made as a sign to the test subject.

In FIG. 1, a CPU substrate 110, a display substrate 120, and a thermal transfer printer 130 are accommodated in a housing of the measuring instrument; the CPU substrate 110 is composed of a microprocessor (CPU) as a main component for controlling the present invention; the display substrate 120 includes a panel mounted thereon to display settings and statuses of the measuring instrument, and the thermal transfer printer 130 prints a result of measurement.

The CPU substrate 110 effects measurement of the present invention by executing a program through the CPU 116 and a RAM/ROM 115 and by controlling various circuits and units disposed on the substrate 110 and on other substrates. A D/A converter 113, an LED drive circuit 111, a sound circuit 112, a data I/O 114, and the like are disposed on the CPU substrate 110, wherein the D/A converter 113 and the LED drive circuit 111 drive LEDs in a goggle 140 covering the eyes of a test subject; the sound circuit 112 makes a buzzer sound as a sign to the test subject, and the data I/O 114 sends measurement data to other computer system and the like. LEDs and the like for displaying the statuses and the like of the the present invention are disposed on the display substrate 120 and the construction and the like of thr display substrate 120 will be explained with reference to FIG. 2. Further, the measuring instrument is supplied with power from an external power supply connected to an inlet 172, thenpower being converted into a direct current having an appropriated voltage by a switching circuit 170.

FIG. 2 is a view showing an outside view (front and back surfaces) of the measuring instrument of the present invention. FIG. 2(a) shows an example of a construction of a panel on the front surface of the measuring instrument. Various setting switches 240, 250, and 270 for setting measurement operations of the instrument, a buzzer volume controller 230, a start button 220, and the like are disposed on the front surface of the instrument. Further, a panel 120 for displaying statuses of the instrument is also disposed on the front surface. A result of measurement is output from the printer 130.

FIG. 2(b) shows an example of a construction of the display panel 120. LED stimulation display lamps 286 and 287, a digital display 281, test subject's response display lamps 282 and 283, and a buzzer display lamp 284 are disposed on the display panel 120, wherein the LED stimulation display lamps 286 and 287 display statuses of the test subject stimulated by the LEDS; the digital display 281 displays the remaining number of times of a series of measurements to be carried out to the test subject and various set information; and the buzzer display lamp 284 is lit during a period in which a buzzer sound is made to notify the test subject of application of stimulation. These displays will be explained in detail in the description of operation of the measuring instrument.

FIG. 2(c) shows an example of a construction of the back surface of the instrument. A connector 182 (for example, RS232C), connectors 152, 162, and 142, and the like are disposed on the back surface, wherein the connector 182 connects the instrument to other instrument; the connector 152 connects a headphone of the test subject to the instrument; the connector 162 connects a switch for detecting a reaction of the test subject to the instrument; and the connector 142 connects the goggle worn by the test subject to the instrument. Further, the inlet 172 for connecting the instrument to the external power supply includes a power supply switch 175, a unit 174 in which a fuse is accommodated, and a power supply connector 173.

Incidentally, in this measuring instrument, eyesight is measured by covering the eyes of the test subject with the goggle 140 and separately irradiating white light from the LEDs in the goggle to the right and left eyes of the test subject. The headphone 150 or a speaker 154 for causing the test subject to hear a buzzer sound (click sound) for calling his or her attention, and a push button switch 160 for detecting a reaction of the test subject are also used. The LEDs for emitting white light are mounted in the goggle 140 in front of the right and left eyes, respectively. These LEDs emit light at an intensity determined under the control of the CPU for an emitting time also determined thereunder. LEDs for emitting white backlight are disposed on the right and left sides of the goggle 140, in addition to the LEDs for emitting white light only for a specific test time. The intensity of the light emitted from the right and left LEDs for test can be changed to three kinds of settings, that is, to a high (H)level, a medium (M) level and a low (L) level which are set by a setting switch 270. The intensity of the light is changed by changing a voltage, which is outputted from the D/A converter 113 and supplied to the LED drive circuit 111, under the control of the CPU 116. In the measuring instrument of the embodiment, the intensity of the stimulation light is set to 0.1, 1, 10 cd/m$^2$ in the low (L) level, to 1, 10, 100 cd/m$^2$ in the medium (M) level, and to 10, 100, 1000 cd/m$^2$ in the high (H) level. Further, the light emission time can be also set to two kinds of times of 0.1, 0.3, 1.0 sec. (×1) and to 0.01, 0.03 sec, 0.1 sec (×0.1) by the setting switch 240. The backlight in the goggle can also be turned ON and OFF by the backlight switch 250. By the way, each photoreceptor cell for sensing light is divided into a rod cell and a pyramid cell depending upon the difference of its outer segment. The pyramid cell relates to the sense of sight in bright light (bright sense of sight), and the rod cell relates to the sense of sight in dim light (twilight sense of sight). Accordingly, the eyesight of bright sense of sight (that is, the pyramid cell) is measured when the backlight (for example, 20 cd/m$^2$) is turned ON, whereas the eyesight of the rod cell+the pyramid cell is measured when the backlight is turned OFF.

Note that it is not necessary to limit the light emission intensity and the light emission time to those exemplified in this embodiment. The number of steps of stimulation and the set number thereof, and specific numerals and the like of the steps of the stimulation can be variously set.

Figure 3:
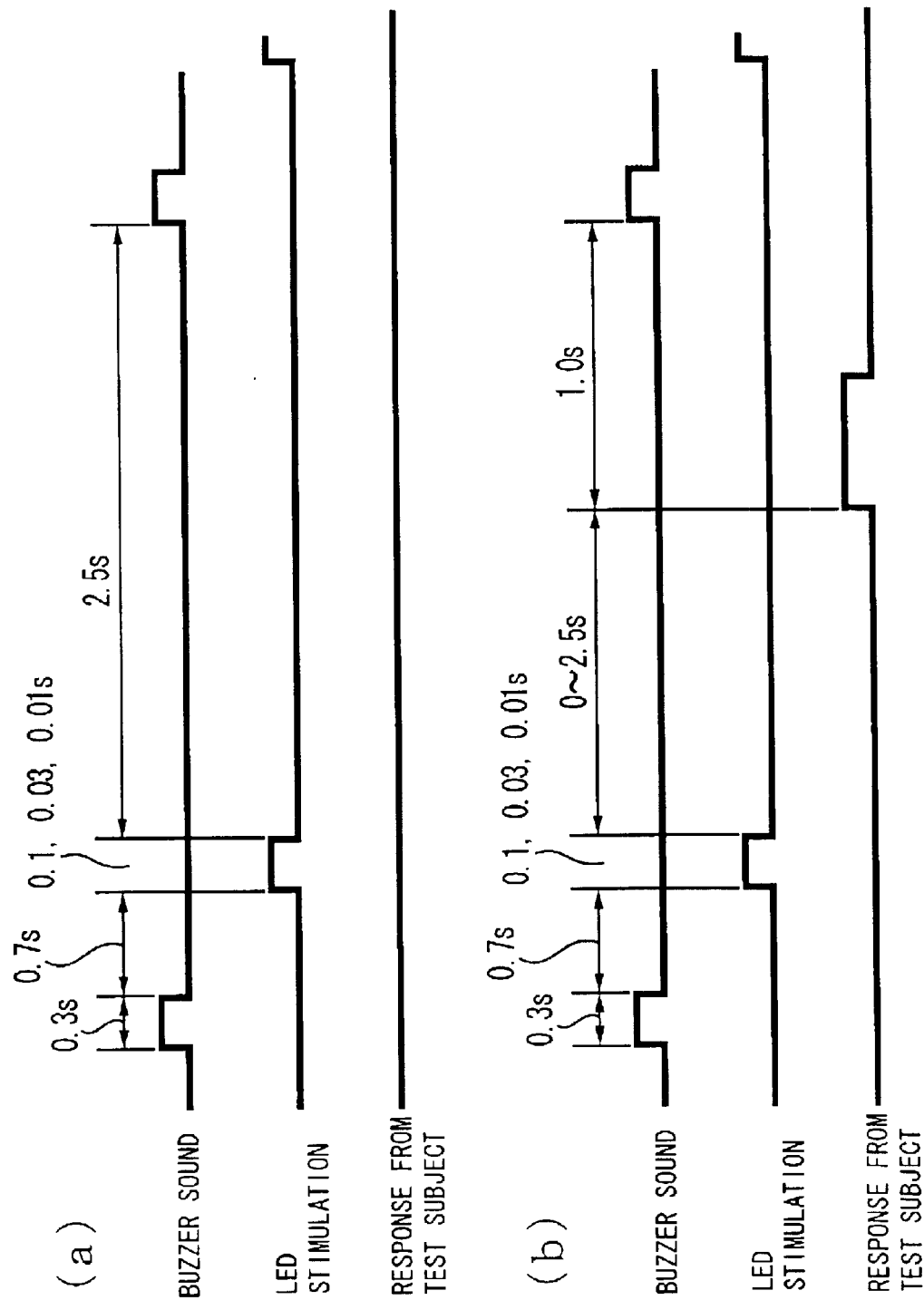
FIG. 3 shows timing charts explaining measurement effected by the poor eyesight measuring instrument of the present invention.

How a test is carried out using the instrument constructed as described above will be explained using FIG. 3. As shown by a time chart shown in FIG. 3(a), the LED in front of the left or right eye in the goggle is emitted at an intensity for an emitting time when 0.7 second, for example, passes after the attention of a test subject is concentrated by making a buzzer sound from the headphone 150, the intensity and the emitting time being selected at random within the range of the setting switches. When the test subject can recognize the emitted light, he or she depresses the push button switch 160. FIG. 3(a) shows an example in which the test subject has not depressed the push button switch 160, whereas FIG. 3(b) shows an example in which the test subject has depressed the push button switch 160. The above reaction is detected by the microprocessor (the CPU 116). A period, during which depression of the push button switch 160 can be detected, is an LED stimulation time (in which the LED is being emitted) and 2.5 seconds until a buzzer sound is made for a next test. When it is detected that the push button switch 160 has been depressed, a buzzer sound is made for the next test in one second after the detection of the depression as shown in FIG. 3(b).

Each LED is emitted at 9 steps in total because three steps are available, respectively for light intensity and light emission time. Further, since the LEDs are provided on the right and left sided, there are 9×2=18 types of light emission is available. Since a case in which the LEDs are not emitted even if a buzzer sound is made is set about 10% in addition to the above, 20 types of emission are available. A reason why the case in which the LEDs do not emit light is provided is to check reliability of the measurement. In the measuring instrument of this embodiment, the number of stimulations effected by emitting light in a series of measurements is set to, for example, 60 times (that is, three times are selected at random at respective steps).

When the measuring instrument can start after it is energized, a test display lamp 260 is lit. When the start switch 220 is depressed after the test display lamp 260 is lit, a series of test (60 times of stimulations by emitted light) is started. Note that when the start button 220 is depressed longer than two seconds while the test is being carried out, the test can be interrupted. A volume of the buzzer sound from the headphone 150 can be adjusted by the buzzer volume controller 230. The light emission time change over switch 240 selects the above-mentioned light emission time from either 0.1, 0.3, 1.0 sec. (×1) or 0.01, 0.03 sec, 0.1 sec (×0.1). The buzzer display lamp 284 is lit while the buzzer sound is being made. The LED stimulation display lamps 286 and 287 show a status in which the test subject is subjected to the LED stimulation and are lit during a period in which the LED stimulation is carried out. Each three pieces of the stimulation display lamps 286 and 287 are disposed and set to L (weak brightness), M (medium brightness), and H (strong brightness) in correspondence to a left eye (LEFT) and a right eye (RIGHT), respectively. When the test subject responds to the LED having been lit by depressing the push button switch 160, the test subject response display lamps 282 or 283 are lit. At that time, the GOOD lamp 282 is lit when the test subject makes a response after the LED is lit. When the test subject makes a response before the LED is lit or even if the LED is not lit, the NG 283 is lit. When the series of measurements is carried out by depressing the start button 220, the digital display 281 displays the remaining number of times of tests.

When the light sensing test is carried out to the total nine kinds of stimulation light resulting from a combination of three steps of brightness and three steps of presented times and the test is repeated three times under the same conditions, the test must be carried out 27 times for each eye, that is, 54 times for both the eyes. Further, when a case of the test in which no light is emitted is included, the test is carried out 60 times. When the right and left eyes are always stimulated 60 times each time a series of test is carried out as described above, a problem is arisen in that the test subject fatigues and a test accuracy is lowered.

In the embodiment, it is contemplated that when light for testing higher sensitivity can be recognized, a test for lower sensitivity can be of course carried out. On the contrary, when light cannot be recognized in a test for low sensitivity, light in a high sensitivity region cannot be moreover recognized. The number of tests for applying stimulation is reduced making use of this principle.

To effect the test according to the principle, test conditions are ranked from conditions for the highest sensitivity toward conditions for lower probability. In the above ranks, when light can be recognized in a test for high sensitivity, tests to be effected under lower conditions of sensitivity are omitted. Inversely, when light for testing low sensitivity cannot be recognized, a test in a region of high sensitivity is omitted. With this test method, a test time can be greatly reduced and a test can be finished simply without a feeling of fatigue. It is needless to say that a test subject, who requires a test of high accuracy, may be subjected to a test including all the standard combinations of steps.

Figure 4:
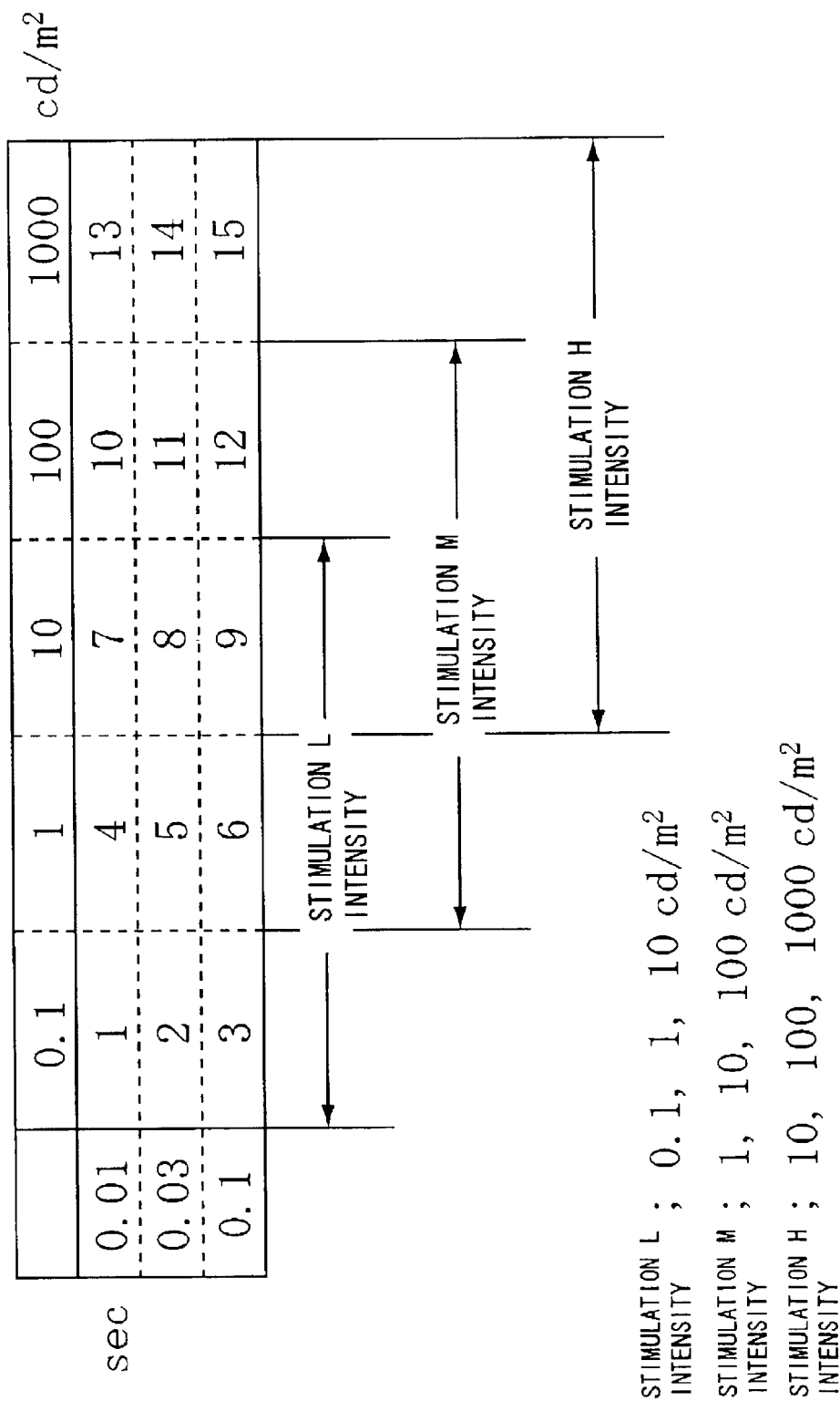
FIG. 4 is a view showing an example of a classification of grades of measurement according to the present invention.

FIG. 4 shows an example of ranks of light sensitivity. FIG. 4 shows a table in which a magnification of a light emitting time is set to ×0.1 with brightness shown by the horizontal axis and a presented time shown by the vertical axis. A highest light sensing rank is represented by "1" and thereafter the ranks are sequentially shown by "2" to "15".

In the ranks set as described above, when a result of test for a light sensing rank "n" can be successively recognized twice, tests for a "n+2" rank and more are omitted. Further, when a result of test for the light sensing rank "n" cannot be successively recognized twice, tests for a rank "n–2" and less are omitted. As shown in FIG. 4, degrees of stimulation intensity can be set in three modes in this measuring instrument of the embodiment. When a light sensing rank "5" can be recognized successively twice in a test of, for example, stimulation intensity L, tests of a rank "7" and more can be omitted. Alternately, when a light sensing rank "4" cannot be successively recognized twice, tests for the rank "2" and less can be omitted.

FIG. 5 shows an example of a result of test effected actually according to the method (number of times of repetition: 3). A symbol "○" shows that light sensitivity could be recognized, a symbol "×" shows that light sensitivity could not be recognized, and "Δ" and "–" show that a test was omitted by the above skip method. That is, "Δ" is regarded as "being viewed", whereas "–" is regarded as "not being viewed. FIG. 5(a) shows a result of test of the right eye (RIGHT), and FIG. 5 shows a result of test of the left eye (LEFT). A term "LoVE SCORE" will be described later. When both the eyes are to be tested entirely in the example of FIG. 5, only 46 times of tests are necessary (as shown by the numeral in the lower right parenthesis of FIG. 5(b) while tests must intrinsically be effected 60 times including six tests in which the eyes are not stimulated due to no light emission. Accordingly, the number of tests can be reduced. Note that the numerals of "ERROR" show that while no light was emitted regardless of that the buzzer was sounded six times, the test subject did not depress the push button even once at that time.

Incidentally, three parameters, that is, brightness of emitted stimulation light, an emission time and the number of times of responses can be obtained in the measuring instrument. When these three parameters are directly regarded as a result of test, it is complex to compare results of the respective tests with each other. When effects of medical treatment and dosing are to be evaluated, an unified evaluation of the effects as in the evaluation of eyesight of the Landolt's bodies of a normal person is understandable even from a standpoint of a patient.

For this purpose, when light can be recognized at least twice in, for example, tests carried out three times under the same conditions, it is regarded as "being viewed", whereas when light can be viewed less than twice, it is regarded as "not being viewed". In the skip method, a result which is obtained in a rank which is higher than the light sensing level of "being viewed" by, for example, at least two ranks, is regarded as "being viewed" while no test is carried out for the rank. Further, a result which is obtained in a rank at least two ranks lower than the light sensing level of "not being viewed" is regarded as "not being viewed" in the same way. Then, a numerical value obtained by adding minus to the numerical value of the condition "not being viewed" among the 15 types of the test conditions is defined as LoVe SCORE. That is, when a result that "being viewed" is obtained in all the 15 types of the test conditions, LoVe SCORE is set to "0", whereas when a result that "not being viewed" is obtained in all the 15 types of the test conditions, LoVe SCORE is set to "–15". While the number of the light sensing level to be skipped is set to the two ranks in the above description, it may be optionally determined.

With the above arrangement, it is possible to provide sixteen types of grades, which is more concrete as compared with the conventional qualitative indicators such as the simple "finger number counting test", "moving finger sensing test", and "light sensing test". Further, quantitative numerals are very convenient when effects of a medical treatment and dosing are evaluated, and an accuracy of evaluation is improved by an increase in the number of classifications.

Figure 6:
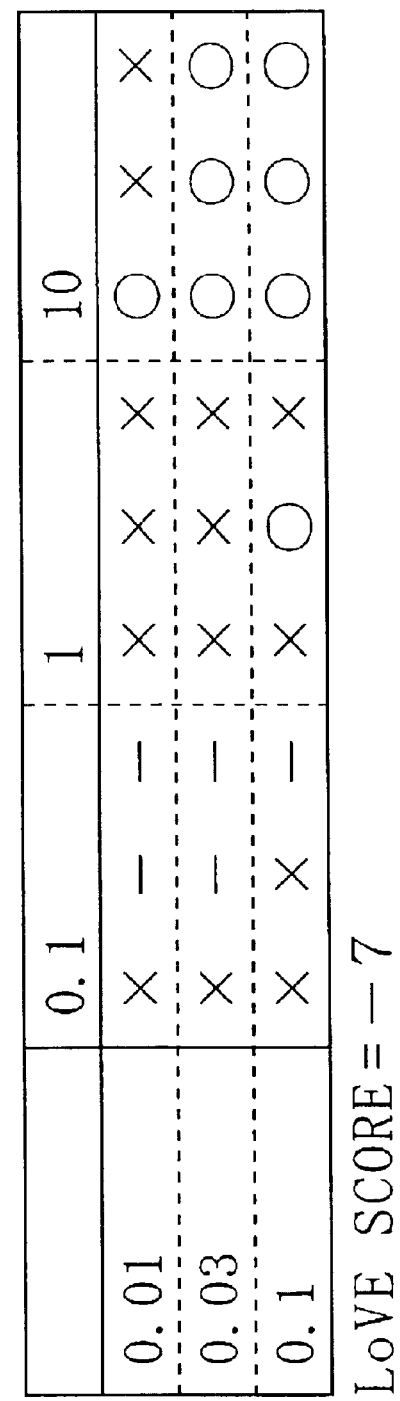
FIG. 6 is a view showing a result of measurement effected by the poor eyesight measuring instrument of the present invention.

FIG. 6 shows an example of a result of test carried out at the stimulation intensity L. Since the light sensing ranks "8" and "9" described in FIG. 4 can be recognized, that is, the light sensing ranks "1" to "7" are not recognized in this case, LOVE SCORE (Low Vision Evaluation Score) is set to "–7".

In the example of FIG. 6, the above-mentioned skip method is also applied using a rank "2", and a light sensing rank "10", which is obtained by adding 2 to a light sensing rank "8" in which light can be viewed (recognized), and ranks more than the light sensing rank "10" are regarded as "being viewed". As a result, LoVE SCORE can be fixed to "–7" without the need of effecting a test at the stimulation intensity M.

In the example of FIG. 6, however, when no light can be viewed in the light sensing rank "8", a test must be carried out at the stimulation intensity M. This is because it cannot be determined from only the result of the test effected at the stimulation intensity L whether or not light can be recognized at the light sensing rank "10". As described above, LoVE SCORE can be obtained by effecting a test using an appropriate combination of the stimulation intensities L, M and H.

LoVE SCORE can be obtained also in a case of FIG. 5 in the same way, wherein the right eye (FIG. 5(a)) is set to "LoVE SCORE "–5" and the left eye (FIG. 5(b)) is set to "LoVE SCORE "–7".

When a result of measurement is printed or displayed, it can also be shown by a three-dimensional graph as shown in FIG. 7(b), in addition to that it is shown in a format of table as shown in FIGS. 5 and 6. FIG. 7(b) shows a case, in which light simulation was confirmed three times in a light sensing rank "15" and once in a light sensing rank "1", by a graph as shown in FIG. 7(a). An overall result of measurement can be easily understood by expressing the result by the graph. Note that LoVE SCORE is set to "–14" in this case.

While the number of times of tests effected in the respective ranks is set to tree times in the above description, the above-mentioned way of thinking is also applicable to a case in which the number times of tests effected in the respective ranks is set to five times. In this case, when light can be viewed at least three times in a certain rank, it is regarded as "being viewed", whereas when it can be viewed less than twice, it is regarded as "not being viewed".

Incidentally, the measuring instrument of the embodiment described in FIGS. 1 and 2 is arranged as a dedicated instrument using the microcomputer. It is possible, however, to construct the poor eyesight measuring instrument of the present invention using a personal computer system. An example of a construction of this case will be described using FIG. 8.

Figure 8:
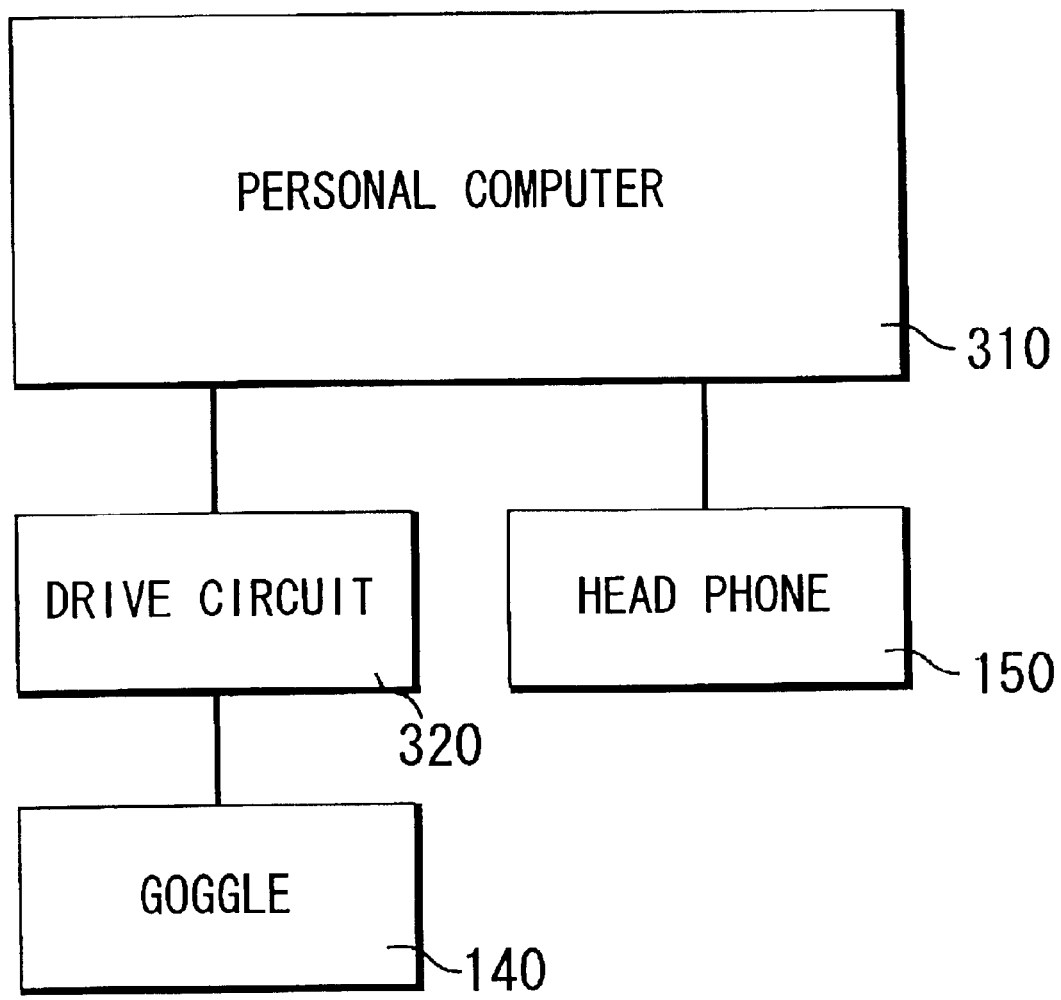
FIG. 8 is a block diagram showing an example of the poor eyesight measuring instrument of the present invention composed of a personal computer system.

In FIG. 8, a drive circuit 320 for driving LEDs in a goggle 140 is connected to a personal computer system 310. The drive circuit may be arranged on a board connected to an internal bus of the personal computer system 310 or may be connected through, for example, an RS232C terminal as an external unit. A headphone 150 for making a sign by a sound is directly connected to a sound mechanism provided with the personal computer system as a standard accessory. The above system construction can realize the above-mentioned measuring instrument by controlling stimulation light, calculating a correct answer rate, graphically showing and printing a result of test, and storing measured data.

Only white LEDs are disposed as the LEDs of the goggle 140 in the above-mentioned measuring instrument. However, even if LEDs of the three primary colors of red, green, and blue are disposed so as to test eyesight for each of the three primary colors (refer to Japanese Unexamined Patent Application Publication No. 11-103259), the above mentioned way of thinking as to the omission of test and the score is also applicable. Note that any device other than, for example, liquid crystal and the like may also be employed to emit white light and light of the three primary colors, in addition to the LED, so long as it can control intensity of light and a light emitting time.

Further, while light stimulation is applied to a test subject after a sound is made in the description of the above-mentioned embodiment, sensible stimulation other than sound (for example, a sign using sense of tough) may be used. When a sign is given by sound, it is difficult to measure a person having poor sense of hearing. However, this problem can be coped with by giving a sign though, for example, a force applied to a skin. Weak electric stimulation may also be applicable.

INDUSTRIAL APPLICABILITY

The above-mentioned poor eyesight measuring instrument can perform a correct test by the smaller number of times of measurements, which can reduce fatigue of a test subject. In addition to the above, a measuring time can be shortened.

Further, objective grades of poor eyesight are defined, results of tests can be easily compared with each other.

What is claimed is:

1. A poor eyesight measuring instrument, comprising:

light emission means for emitting light to each or right and left eyes;

light emission control means for controlling said light emission means according to light stimulation steps defined by a combination of light intensities and light emission times; and means for detecting presence or absence of reaction of a test subject to light at the respective stimulation steps, wherein, said light emission control means controls selection of the stimulation steps at random in a series of tests effected a prescribed number of times at each stimulation step; wherein, said light emission control means controls selection of the stimulation steps at random in a series of tests effected a prescribed number of times at each stimulation step;

when said light emission control means detects reactions, the number of times of which is a predetermined number of times and less, at a given stimulation step, said light emission control means regards the given stimulation step as not being viewed and omits tests which would be effected at stimulation steps lower than the given stimulation step by a predetermined number of steps; and when said light emission control means detects reactions, the number times of which is a predetermined number of times and more, at a given stimulation step, said light emission control means regards the given stimulation step as being viewed and omits tests which would be effected at stimulation steps higher than the given stimulation step by a predetermined number of steps.

2. A poor eyesight measuring instrument according to claim 1, further comprising means for outputting a total number of the not viewed stimulation steps as an evaluation of poor eyesight.

3. A poor eyesight measuring instrument according to claim 1, wherein said light emission means emits white light.

4. A poor eyesight measuring instrument according to claim 3, wherein said light emission means further emits the three primary colors of red, green, and blue.

5. A poor eyesight measuring instrument according to claim 1, wherein said light emission means comprises any of an LED, a liquid crystal, and a cathode ray tube.

6. A poor eyesight measuring instrument according to claim 1, further comprising backlight emission means for emitting back light.

7. A poor eyesight measuring instrument according to claim 1, further comprising means for giving a sign, and said light emission control means controls light emission so that light is emitted after a sign is given.

8. A poor eyesight measuring instrument according to claim 7, wherein said light emission control means includes control for not emitting light after a sign is given.

9. A poor eyesight measuring instrument according to claim 7, wherein said means for giving a sign gives a sound.

10. A poor eyesight measuring method, comprising the steps of:

emitting light to each of right and left eyes;

controlling the emission of light according to light stimulation steps defined by a combination of light intensities and light emission times; and detecting presence or absence of reaction of a test subject to light at the respective stimulation steps;

regarding, when reactions, the number of times of occurrence of which is a predetermined number of times of occurrence and less, are detected at a given stimulation step, the given stimulation step as not being viewed and omitting tests which would be effected at stimulation steps lower than the given stimulation step by a predetermined number of steps; and regarding, when reactions, the number of times of occurrence of which is a predetermined number of times of occurrence and more, are detected at a given stimulation step, the given stimulation step as being viewed and omitting tests which would be effected at stimulation steps higher than the given stimulation step by a predetermined number of steps.

11. A poor eyesight measuring method according to claim 10, further comprising the step of outputting a total number of the not viewed stimulation steps as an evaluation of poor eyesight.

* * * * *